United States Patent [19]

Gach

[11] Patent Number: 4,890,734
[45] Date of Patent: Jan. 2, 1990

[54] DISPOSABLE HOLDER FOR HYPODERMIC NEEDLES AND SHEATHS

[76] Inventor: Jerald Gach, 5385 Terence Ct., Bloomfield Hills, Mich. 48013

[21] Appl. No.: 311,112

[22] Filed: Feb. 15, 1989

[51] Int. Cl.⁴ .......................................... A65D 83/10
[52] U.S. Cl. ................................. 206/366; 206/438; 220/17; 128/919
[58] Field of Search ............... 206/363, 364, 366, 438; 220/17; 128/919

[56] References Cited

U.S. PATENT DOCUMENTS

| | | | |
|---|---|---|---|
| 4,351,434 | 9/1982 | Elisha .................................. | 206/366 |
| 4,494,652 | 1/1985 | Nelson et al. ......................... | 206/366 |
| 4,658,957 | 4/1987 | Guth et al. ............................ | 206/366 |
| 4,802,579 | 2/1989 | Hall et al. ............................. | 206/366 |
| 4,807,344 | 2/1989 | Kelson et al. ......................... | 206/366 |
| 4,826,073 | 5/1989 | Bruno .................................. | 206/366 |

*Primary Examiner*—Joseph Man-Fu Moy
*Attorney, Agent, or Firm*—Brooks & Kushman

[57] ABSTRACT

A disposable holder (10) for hypodermic needles (12) and sheaths (14) is disclosed as having a base (16), walls (26, 36, 38, 48) extending upwardly from the base (16), and a roof (58) extending between the walls spaced apart from and above the base (16). A storage location (60) is defined between the walls (26, 36, 38, 48), and base (16), and the roof (58). Defined in the roof (58) is a plurality of disposal orifices (62) communicating with the storage location (60) and allowing passage via the disposal orifices (62) into the storage location (60) of the hypodermic needles (12) and sheaths (14) for safe discarding in the holder (10) after use. A plurality of retaining orifices (64) for engaging the needles (12) and sheaths (14) in an interim storage position are also defined in the roof (58) for safe securement of the needles (12) and sheaths (14) for stability and ease of access between uses.

14 Claims, 1 Drawing Sheet

U.S. Patent
Jan. 2, 1990
4,890,734
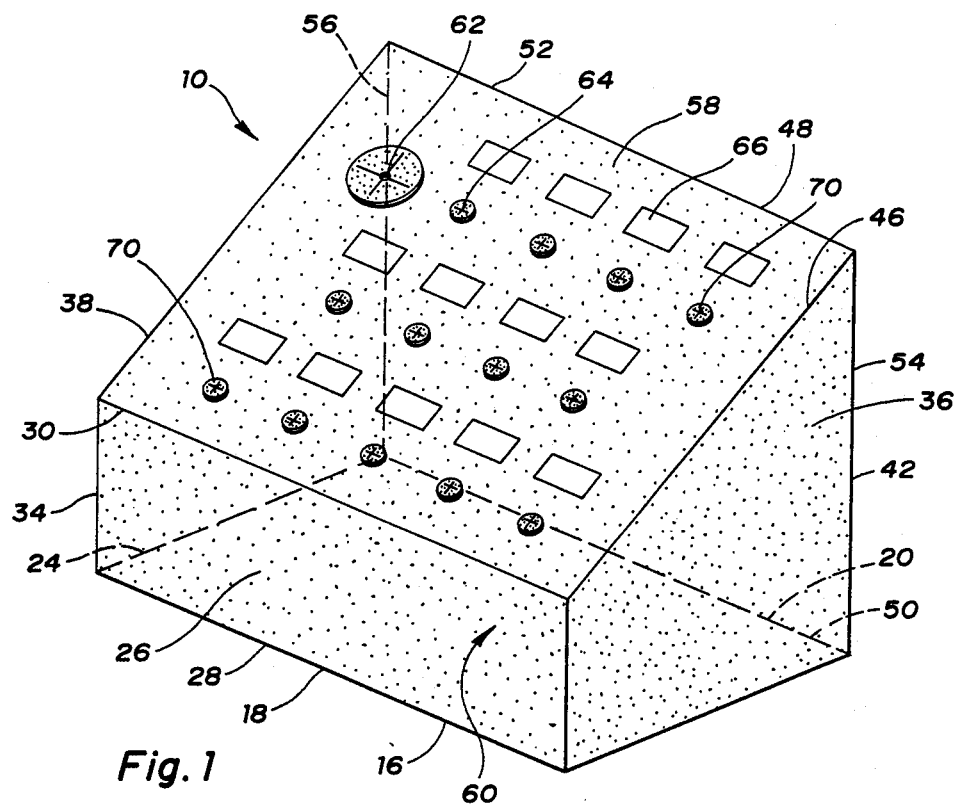
Fig. 1
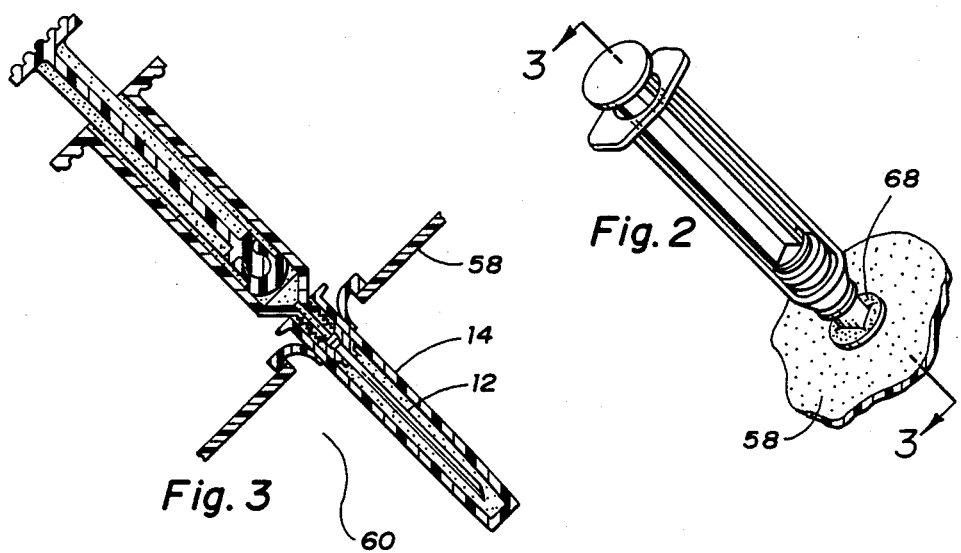
Fig. 2
Fig. 3

DISPOSABLE HOLDER FOR HYPODERMIC NEEDLES AND SHEATHS

TECHNICAL FIELD

The present invention relates to a hypodermic needle and sheath holder, and more particularly concerns a holder which not only retains hypodermic needles safely between uses, but also allows for disposal of the hypodermic needle in such a manner as to prevent puncture and contamination of personnel.

BACKGROUND ART

The epidemic of Acquired Immunodeficiency Syndrome (AIDS) has led to intense concern among health care workers about the risks they face in the hospital environment. Infections in health care workers have been attributed to needle-stick injuries. With needle-stick injuries in particular, despite safety guidelines and employee education, there is little evidence that the incidence of injury and contamination is abating. The potential medical and psychological consequences of needle sticks for health care workers and their spouses or sexual partners remain great.

Against this background, the National Academy of Sciences Committee on Trauma Research has concluded that improvements in product design are among the most successful approaches to the prevention of injury.

Many injuries are related to re-capping, or replacing a needle into a sheath. Contributing to these injuries is the risk of disassembling a device with an uncapped, contaminated needle and the difficulty of safely carrying several uncapped items to a disposal box in a single trip. Employees often attempt to dispose of accumulated debris by making a single trip to a trash container to avoid interrupting a medical procedure. Injuries then occur when workers pick up the debris or fumble with it in transit to the disposal box.

In practice, most problems with needle sticks occur after the needle has been used and before its disposal. Inadvertent skin penetration can occur while the needle is being recapped, when the sharp point penetrates a finger or thumb that is holding the needle sheath steady, either because the cap is missed or the cap is pierced. To avoid either risk, the free hand must be kept away from the path of an advancing and potentially contaminated needle tip. Also, inadvertent penetration can result from contact with the needle while the needle lies on an exposed surface, or during disassembly of the needle from the sheath, or because the sheath falls off after recapping.

During or after disposal, inadvertent skin penetration can result because a needle protrudes from trash, or while introducing the needle into the disposal box.

It would be desirable to produce a safe device for manipulating and disposing of needles which effects significant cost savings. In the United States for the year 1984, the average cost of a needle-stick injury, including costs of laboratory tests and time lost, but not the cost of treatment with immune globulin, was $64.50. Such funds could be put to better use, such as for the provision of hepatitis vaccine to susceptible personnel.

In light of the aforementioned problems, several solutions have been attempted. One is exemplified in U.S. Pat. No. 4,753,345. This patent discloses a hypodermic syringe tray which is adapted to hold at least one hypodermic syringe so as to secure the syringe and its cover during thermal sterilization. However, this approach holds the needle and sheath horizontally in close juxtaposition with adjacent needles, thereby rendering access and manipulation of each needle quite awkward. Another approach is exemplified by U.S. Pat. No. 4,742,910. This patent discloses a needle sheath holder with a hollow barrel member having an open upper end. In this approach, a needle sheath holder is hand-held, and is set on a stand next to the patient or set in a test tube rack. Following this approach, however, there is difficulty in handling a series of needles for efficiency in use. Moreover, setting the needle sheath holder in a test tube rack produces instability when the rack is inclined to a vertical position for ease of access to the needle sheath holder. Problems of disposal remain unsolved.

Despite efforts to solve problems of unwanted disease transmission through needle-stick, the results are still disappointing. The optimal solution appears to be to design devices which allow the needle to remain covered at all times, except during actual use. At a minimum, a fixed barrier should be provided between the hands and the needle after use.

It would be preferable to allow or require the worker's hands to remain behind the needle as it is covered to preclude the movement of the hands in the direction of used needles, as in recapping. To provide the greatest benefit, such a safety feature should be an integral part of the device and not an accessory item to be used optionally in combination with a hazardous item such as an infected needle. In this way, the integral safety feature remains in place precisely when and where it is needed. Moreover, the safety feature should be in effect before disassembly and should remain in effect after disposal, thus protecting the trash handler as well as the user. Finally, safety features should be as simple as possible and should require little or no training to use effectively.

Those skilled in the art may opine that the safest place for a used hypodermic needle is in its cover. However, recapping, with or without a guard, requires the movement of the hands toward a contaminated needle, which is an inherently risky maneuver. It would therefore be desirable to have a device which does not require the movement of hands toward a contaminated needle during the recapping operation, while being simple enough to use without special training or additional equipment.

DISCLOSURE OF INVENTION

An object of the present invention is to provide an improved disposable holder for hypodermic needles and sheaths having advantages which were not heretofore possible.

In carrying out the above and other objects, the hypodermic needle and sheath holder of the present invention comprises a base, an anterior and posterior wall extending upwardly from the base, and a pair of opposing side walls also extending upwardly from the base. Extending between the top edges of the walls is a roof in which is defined a plurality of disposal and retaining orifices.

Each disposal orifices communicates with a storage location defined between the roof, the base, and the walls. The disposal orifices allow passage into the storage location of the hypodermic needle and sheath for safe discarding in the holder after use. Each retaining orifice engages the hypodermic needle and sheath in an interim storage position for safety, stability, and ease of access between uses.

In a preferred embodiment of the present invention, the anterior wall extends a shorter distance upwards from the base than the posterior wall, so that the roof is inclined with respect to the base. This facilitates insertion and removal of the hypodermic needles and sheath holders into and from the orifices defined in the roof.

Each retaining orifice receives only one hypodermic needle and sheath at a time so that a series of hypodermic needles and sheaths are gripped, with the hypodermic needles and sheaths extending through the roof into the storage location for protection of the user and preservation of sterility when the hypodermic needle is not in use.

In an alternate embodiment, the roof of the holder has indicia for each of the retaining orifices which correspond to the contents of, or intended use for, medicinal fluid contained in the hypodermic needle.

In use, the present invention also contemplates a method for manipulating hypodermic needles and holders. The method comprises the steps of inserting a needle capped in its sheath into a retaining orifice in the holder so that the sheath is gripped by the retaining orifice. The needle is then removed from the sheath and the retaining orifice for administration to a patient requiring medicinal fluid, the sheath remaining in the retaining orifice while the needle is in use. Next, the needle is replaced after use into the sheath without the hand of the user being exposed to the used needle.

For disposal, the sheath and capped needle are removed from the retaining orifice and are inserted into a disposal orifice for passage into a storage location below the roof of the holder. For safe disposal, the hypodermic needle and sheath holder is discarded, together with its contents of used needles and holders, into a trash receptacle. In this way, a worker is not exposed to risk of contamination by needle-stick because contaminated needles are confined to the storage location within the holder.

Further objects, features, and advantages of the invention will become apparent from a consideration of the following description of the best mode for carrying out the invention when taken in conjunction with the appended claims and the accompanying drawing.

BRIEF DESCRIPTION OF DRAWINGS

FIG. 1 is a front right perspective view of a hypodermic needle and sheath holder of the present invention:

FIG. 2 is a perspective view of a hypodermic syringe with its needle and sheath extending into and through a retaining orifice defined in a roof of the holder of the present invention; and FIG. 3 is a vertical sectional view taken along the line 3—3 of FIG. 2 showing a hypodermic syringe, needle, and holder inserted through a retaining orifice defined in the roof of the holder.

BEST MODE FOR CARRYING OUT THE INVENTION

With reference to FIGS. 1-3 of the drawing, an improved disposable hypodermic needle and sheath holder constructed in accordance with the present invention is generally indicated by the reference numeral 10. The holder 10 includes a base 16, an anterior wall 26 extending upwardly from the base 16, and a posterior wall 48 also extending upwardly from the base 16. A pair of opposing side walls 36, 38 also extend upwardly from the base and extend between the anterior and posterior walls 26, 48.

The base 16 has a front edge 18, a back edge 20 opposing the front edge 18, and a pair of opposing side edges 22, 24 which extend between the front and back edges 18, 20.

The anterior wall 26 extends upwardly from the front edge 18 of the base 16. Also included in the anterior wall 26 is a bottom edge 28 connected to the front edge 18 of the base 16, a top edge 30, and a pair of opposing lateral edges 32, 34 extending between the bottom edge 28 and the top edge 30.

The pair of side walls 36, 38 extend upwardly from the associated side edges 22, 24 of the base 16. Each side wall 36, 38 has a forward edge 40 connected to one of the lateral edges 32, 34 of the anterior wall 26, a rearward edge 42 opposing the forward edge 40, and a basal edge 44 connected to one of the side edges 22, 24 of the base 16. An upper edge 46 opposes the basal edge 44.

Opposing the anterior wall 26 is a posterior wall 48 which extends upwardly from the back edge 20 of the base 16. The posterior wall 48 has a bottom edge 50 connected to the back edge 20 of the base 16, a top edge 52, and a pair of opposing lateral edges 54, 56. The posterior wall 48 extends upwardly from the back edge 20 of the base 16. The posterior wall 48 has a bottom edge 50 connected to the back edge 20 of the base 16, a top edge 52, and a pair of opposing lateral edges 54, 56 extending between the bottom edge 50 and the top edge 52.

A roof 58 extends between the top edge 52 of the posterior wall 48, the base 16, the anterior wall 26, and the pair of side walls 36, 38. Defined between the base 16, the walls, and the roof 58 is a storage location 60. Within the roof 58 is a plurality of disposal orifices 62 communicating with the storage location 60 and allowing passage into the storage location 60 of the hypodermic needles 12 and sheaths 14 for safe discarding in the holder 10 after use. A plurality of retaining orifices 64 are also defined within the roof 58. The retaining orifices 64 engage the hypodermic needles 12 and sheaths 14 in an interim storage position for safety, stability, and ease of access between uses.

In a preferred embodiment of the invention, the anterior wall 26 extends a shorter distance upwards from the base 16 than the posterior wall 48 so that the roof 58 is inclined with respect to the base 16 to facilitate insertion and removal of the hypodermic needles 12 and sheaths 14 into and from the orifices 62, 64 defined in the roof 58. In use, it has been found that the sloping roof 58 of the holder 10 provides for ease of access by a worker who typically manipulates hypodermic needles and sheaths from a position in front of and above the holder 10. Good results are achieved where the roof 58 is inclined upwardly from the top edge 30 of the anterior wall 26 at about a 45° angle with respect to the base 16. In this way, there is provided a means for retaining a syringe, a needle, and its holder in an inclined position between usage which permits both ready visual inspection and ease of manipulation.

In the preferred embodiment, it has proven useful to make the holder 10 such that the top edge 52 of the posterior wall 48 is about 3 inches above the base 16 and the top edge 30 of the anterior wall 26 is about 7 inches above the base 16. By constructing the holder 10 with these approximate dimensions, it has been found that the hypodermic needles and sheaths can be inserted through any of the disposal orifices for ready passage into the storage location 60 without first being impeded by contact between the sheath 14 and the base 16. In this embodiment, the length of the top edge 30 of the anterior wall 26 is between about 8 and 10 inches, and the base 16 measures 8-10 inches by about 5 inches. In practice, it has been found that by constructing the invention disclosed with these approximate dimensions, the hypodermic needle 12 and sheath 14 can be inserted into any of the available retaining orifices for gripping thereby without the sheath 14 impacting the base 16.

Following the teachings of this invention, the hypodermic needle and sheath holder 10 supports and stores a plurality of hypodermic needles 12 and sheaths 14 of a selected size in a manner which prevents damage thereto or to the user as well as maintaining the needles 12 and sheaths 14 in an orderly relationship.

In the preferred embodiment, the plurality of disposal orifices 62 and retaining orifices 64 are deployed in spaced rows generally parallel to the anterior wall 26. As best shown in FIG. 1, the alignment of orifices 62, 64 is staggered between adjacent rows. In this way, a needle 12 and sheath 14 inserted, for example, in a retaining orifice 64 located in the middle row will be positioned below and between the retaining orifices 64 included in the spaced rows above and below the middle row. It has been found that such a spacial relationship between the orifices 62, 64 permits ready visual inspection of the needles 12 and sheaths 14 between uses, while facilitating manipulation. The retaining orifices 64 are of a size sufficient to engage and retain the hypodermic needle 12 and sheaths 14 adjacent to the roof 58 of the holder 10. The disposal orifices 62 are of a size sufficient to allow passage herethrough of the hypodermic needle 12 and sheath 14 into the storage location 60 of the holder 10.

Like the disposal orifices 62, the retaining orifices 64 each receive only one hypodermic needle 12 and sheath 14 at a time so that a series of hypodermic needles 12 and sheaths 14 are retained by selected retaining orifices 64 with the needles 12 and sheaths 14 extending downwardly through the roof 58 into the storage location 60 for protection of the user when the hypodermic needle 12 is not in use.

In another embodiment of the invention, the roof 58 of the holder 10 has indicia 66 for each of the retaining orifices 64. The indicia 66 correspond to the contents of, or intended use for medicinal fluid contained in the hypodermic needle 12.

In yet another embodiment of the invention, each of the orifices 62, 64 is generally circular and includes a cap 70 with a plurality of slits 68 radiating from the center of the orifice. The slits 68 defined within the cap 70 are flexible and extend downwardly into the storage location 60 below the roof 58 upon the application of pressure by a needle 12 in its sheath 14. In this way, the hypodermic needle 12 and sheath 14 can be selectively retained by or removed from the retaining orifice 64.

The present invention also contemplates a method for manipulating hypodermic needles 12 and sheaths 14 in combination with the holder 10. The method comprises the steps of inserting a needle 12 capped in its sheath 14 into a retaining orifice 64 so that the sheath 14 is gripped by the retaining orifice 64. The needle 12 is then removed from the sheath 14 and the retaining orifice 64 for administration to a patient requiring medicinal fluid, the sheath 14 remaining in the retaining orifice 64 while the needle 12 is in use. Next, the needle 12 is replaced after use into the sheath 14 without the hand of the user being exposed to the used needle 12.

Alternatively, following the teachings of the present invention, the method of manipulating needles 12 may include the further step of removing the sheath 14 and capped needle 12 from the retaining orifice 64 for safe disposal. Next, both the sheath 14 and the needle 12 are inserted into a disposal orifice 62 for passage into the storage location 60 below the roof 58.

Safe disposal of the needles 12 and sheaths 14 is achieved by following the additional step of discarding the holder 10 and its contents of used needles 12 and sheaths 14 into a trash receptacle so that a worker is not exposed to risk of contamination by needle-stick because contaminated needles 12 are confined to the storage location 60 within the holder 10. If desired, the orifices 62, 64 in the roof 58 can be taped over after needles 12 and sheaths 14 have been inserted into the storage location 60 before disposal of the holder 10 and its potentially contaminated contents.

While the best mode for carrying out the invention has been described in detail, those familiar with the art to which this invention relates will recognize various alternative designs and embodiments for practicing the invention as disclosed by the following claims.

What is claimed is:

1. A hypodermic needle and sheath holder comprising:

a base having a front edge, a back edge opposing the front edge, and a pair of opposing side edges extending between the front and back edges;

an anterior wall extending upwardly from the front edge of the base, the anterior wall having a bottom edge connected to the front edge of the base, a top edge, and a pair of opposing lateral edges extending between the bottom edge and the top edge of the anterior wall;

a pair of side walls, each side wall extending upwardly from the associated side edges of the base, each side wall having a forward edge connected to one of the lateral edges of the anterior wall, a rearward edge opposing the forward edge, a basal edge connected to one of the side edges of the base, and an upper edge opposing the basal edge;

a posterior wall extending upwardly from the back edge of the base, the posterior wall having a bottom edge connected to the back edge of the base, a top edge, and a pair of opposing lateral edges extending between the bottom edge and the top edge of the posterior wall; and a roof extending between the top edge of the anterior wall and the top edge of the posterior wall, the base, the anterior wall, the pair of side walls, the posterior wall and the roof defining therebetween a storage location, the roof defining a plurality of disposal orifices communicating with the storage location and allowing passage into the storage location of the hypodermic needles and sheaths for safe discarding in the holder after use; and a plurality of retaining orifices for engaging the hypodermic needles and sheaths in an interim storage position for safety, stability, and ease of access between uses.

2. The hypodermic needle and sheath holder of claim 1, wherein the anterior wall extends a shorter distance upwards from the base than the posterior wall so that the roof is inclined with respect to the base to facilitate insertion and removal of the hypodermic needles and sheath holders into and from the orifices defined in the roof.

3. The hypodermic needle and sheath holder of claim 2, wherein the roof is inclined upwardly from the top edge of the anterior wall at about a 45 degree angle with respect to the base.

4. The hypodermic needle and sheath holder of claim 1, wherein the top edge of the posterior wall is about 3 inches above the base and the top edge of the anterior wall is about 7 inches above the base so that the hypodermic needle and sheath can be inserted through one of the disposal orifices for passage into the storage location.

5. A hypodermic needle and sheath holder for supporting and storing a plurality of hypodermic needles and sheaths of a selected size in a manner to prevent damage thereto or to user as well as to maintain the hypodermic needles and sheaths in an orderly relationship, the holder comprising:
  a base having a front edge, a back edge opposing the front edge, and a pair of opposing side edges extending between the front and back edges;
  an anterior wall extending upwardly from the front edge of the base, the anterior wall having a bottom edge connected to the front edge of the base, a top edge, and a pair of opposing lateral edges extending between the bottom edge and the top edge of the anterior wall;
  a pair of side walls, each side wall extending upwardly from the associated side edge of the base, each side wall having a forward edge connected to one of the lateral edges of the anterior wall, a rearward edge opposing the forward edge, a basal edge connected to one of the side edges of the base, and an upper edge opposing the basal edge;
  a posterior wall extending upwardly from the back edge of the base, the posterior wall having a bottom edge connected to the back edge of the base, a top edge, and a pair of opposing lateral edges extending between the bottom edge and the top edge of the posterior wall; and
  a roof extending between the top edge of the anterior wall and the top edge of the posterior wall, the base, the anterior wall, the pair of side walls, the posterior wall and the roof defining therebetween a storage location, the roof defining
  a plurality of disposal orifices communicating with the storage location and allowing passage into the storage location of the hypodermic needles and sheaths for safe discarding in the holder after use; and
  a plurality of retaining orifices for engaging the hypodermic needles and sheaths in an interim storage position for stability and ease of access between uses.

6. The hypodermic needle and sheath holder of claims 1 or 5, wherein the plurality of orifices are disposed in spaced rows generally parallel to the anterior wall.

7. The hypodermic needle and sheath holder of claims 1 or 5, wherein the retaining orifices are of a size sufficient to engage and retain the hypodermic needle and sheath adjacent to the roof of the holder.

8. The hypodermic needle and sheath holder of claims 1 or 5, wherein the disposal orifices are of a size sufficient to allow passage therethrough of the hypodermic needle and sheath into the storage location of the holder.

9. The hypodermic needle and sheath holder of claims 1 or 5, wherein the retaining orifices each receive only one hypodermic needle and sheath at a time so that a series of hypodermic needles and sheaths are retained by selected retaining orifices with the hypodermic needles and sheaths extending downwardly through the roof into the storage location for protection of the user when the hypodermic needle is not in use.

10. The hypodermic needle and sheath holder of claims 1 or 5, in which the roof of the holder has indicia for each of the retaining orifices, the indicia correspond to the contents of, or intended use for medicinal fluid contained in the hypodermic needle.

11. The hypodermic needle and sheath holder of claims 1 or 5, each retaining orifice being generally circular, and including a plurality of slits radiating from the center of the orifice so that the hypodermic needle and sheath can be selectively retained by or removed from the orifice.

12. A method for manipulating hypodermic needles and sheaths in combination with a holder for said hypodermic needles and sheaths, the holder including:
  a roof extending between an anterior wall, a posterior wall, and a pair of side walls, the walls extending upwardly from a base, the walls, the base, and the roof defining therebetween a storage location, the roof defining
  a plurality of disposal orifices communicating with the storage location and allowing passage into the storage location of the hypodermic needles and sheaths for safe discarding in the holder after use; and
  a plurality of retaining orifices for engaging the hypodermic needles and sheaths in an interim storage position for stability and ease of access between uses, the method for manipulating hypodermic needles and sheaths comprising the steps of:
  inserting a needle capped in its sheath into a retaining orifice so that the sheath is gripped by the retaining orifice;
  removing the needle from the sheath and the retaining orifice for administration to a patient requiring medicinal fluid, the sheath remaining in the retaining orifice while the needle is in use;
  replacing the needle after use into the sheath without the hand of the user being exposed to the used needle.

13. The method of claim 12, further including the steps of:
  removing the sheath and capped needle from the retaining orifice for safe disposal;
  inserting the sheath and needle into a disposal orifice for passage into the storage location below the roof.

14. The method of claim 13, further including the step of:
  discarding the hypodermic needle and sheath holder and its contents of used needles and sheaths into a trash receptacle so that a worker is not exposed to risk of contamination by needle stick because contaminated needles are confined to the storage location within the holder.

* * * * *